(12) United States Patent
Lewis et al.

(10) Patent No.: US 10,959,858 B2
(45) Date of Patent: Mar. 30, 2021

(54) ORTHOPEDIC IMPLANT INSERTION INSTRUMENT

(71) Applicant: Bio2 Technologies, Inc., Woburn, MA (US)

(72) Inventors: Casey S Lewis, Medford, MA (US); Janet L Krevolin, Somerville, MA (US); Barry Fell, Hummelstown, PA (US)

(73) Assignee: NOVUM MEDICAL, INC., Woburn, MA (US)

( * ) Notice: Subject to any disclaimer, the term of this patent is extended or adjusted under 35 U.S.C. 154(b) by 256 days.

(21) Appl. No.: 15/926,017

(22) Filed: Mar. 20, 2018

(65) Prior Publication Data
US 2018/0360622 A1  Dec. 20, 2018

Related U.S. Application Data

(60) Provisional application No. 62/474,450, filed on Mar. 21, 2017.

(51) Int. Cl.
*A61F 2/46* (2006.01)
*A61F 2/30* (2006.01)

(52) U.S. Cl.
CPC ... *A61F 2/4611* (2013.01); *A61F 2002/30604* (2013.01); *A61F 2002/4622* (2013.01); *A61F 2002/4627* (2013.01); *A61F 2002/4628* (2013.01); *A61F 2002/4681* (2013.01)

(58) Field of Classification Search
CPC ............ A61F 2/4611; A61F 2002/4622
See application file for complete search history.

(56) References Cited

U.S. PATENT DOCUMENTS

2006/0030856 A1* 2/2006 Drewry ............... A61F 2/447
606/90

* cited by examiner

*Primary Examiner* — Olivia C Chang (57) ABSTRACT

An insertion instrument for inserting an implant in an intervertebral space is provided. The instrument includes a housing with an inner shaft with a device holder on the distal end and a locking lever on a shaft pin on the proximate end. The device holder has a gripping surface that engages the implant through an actuating mechanism through the locking lever. The instrument is operable to insert the implant into a vertebral space through impaction and is extracted without disturbing the placement of the implant.

12 Claims, 7 Drawing Sheets

ORTHOPEDIC IMPLANT INSERTION INSTRUMENT

CROSS REFERENCE TO RELATED APPLICATION

This application claims the benefit of U.S. Provisional Application No. 62/474,450, filed Mar. 21, 2017.

FIELD OF THE INVENTION

The present invention generally relates to medical devices and implants for the spine. In particular, the present invention relates to minimally invasive, lightweight instruments for the insertion of an interbody device between adjacent vertebrae during surgery of a patient's spine.

BACKGROUND OF THE INVENTION

Spinal fusion surgery involves the addition of bone graft to the area of the spine to set up a biological response that causes bone to grow between two adjacent vertebral elements to stop motion of the spine at that segment. Spinal fusion surgery, such as posterior lumbar interbody fusion, can achieve fusion of adjacent vertebrae with the insertion of a cage or spacer directly into the disc space. The spacer maintains the desired distance between the vertebral body segments which avoids impingement of nerves to reduce back pain.

Surgery is an ordeal and to minimize the invasiveness of the procedure on the patient an orthopedic surgeon would prefer to perform the surgery with the smallest possible incision required to implant the device. As such, there is a need for a lightweight interbody device insertion instrument that delivers the device with surgical techniques that are minimally invasive for the patient and affords more precision for the surgeon while implanting the device.

BRIEF SUMMARY OF THE INVENTION

According to one aspect of the invention, an instrument is provided. The instrument includes a device holder on an inner shaft that is configured for relative translation within a housing. A locking lever, rotatably attached to the inner shaft translates the inner shaft to reduce the spacing of the device holder thereby securing the device therein.

BRIEF DESCRIPTION OF THE SEVERAL VIEWS OF THE DRAWING

The foregoing and other objects, features, and advantages of the invention will be apparent from the following detailed description of the several embodiments of the invention, as illustrated in the accompanying drawings in which like reference characters refer to the same parts throughout the different views. The drawings are not necessarily to scale, with emphasis instead being placed upon illustrating the principles of the invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

The present invention provides an insertion instrument for the insertion of an interbody device (IBD) or other orthopedic implantable device during surgery that requires accurate placement that may also require the application of force or impact when implanted.

Figure 1:
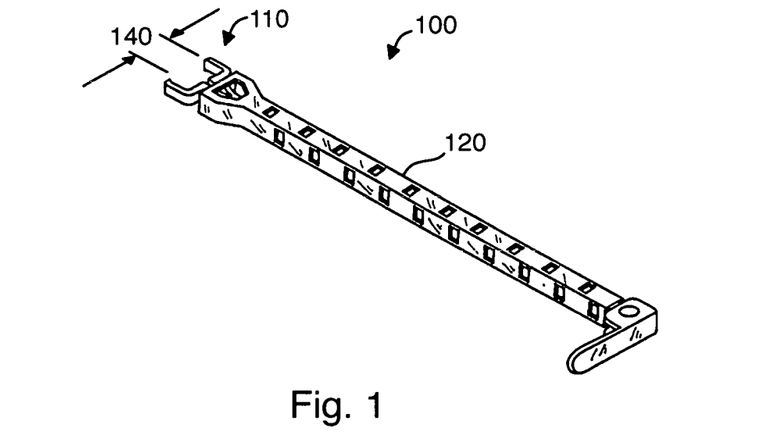
FIG. 1 is an isometric view of the insertion instrument according to the present invention in its undeployed state.

Turning to FIG. 1 there is shown an insertion instrument 100 according to the present invention. The insertion instrument 100 includes a device holder 110 at a distal end, a housing 120, and a locking lever 130 at the proximate end. The insertion instrument 100 as shown in FIG. 1 is in an undeployed condition where the undeployed spacing 140 is greater than the spacing required to hold the IBD or orthopedic device or implant.

Figure 2:
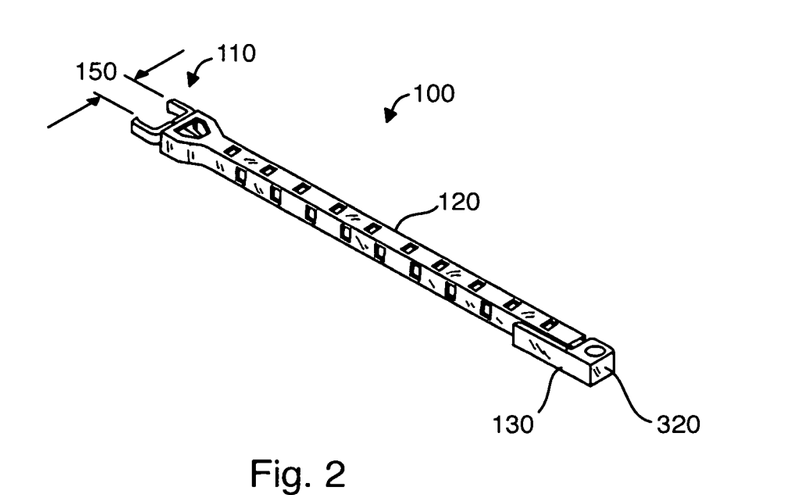
FIG. 2 is an isometric view of the insertion instrument according to the present invention in its deployed state.

FIG. 2 depicts the insertion instrument 100 in a deployed condition (with the IBD implant not shown for clarity), wherein the deployed spacing 150 is adapted to sufficiently grip the desired IBD implant for insertion into the patient during surgery.

Figure 3:
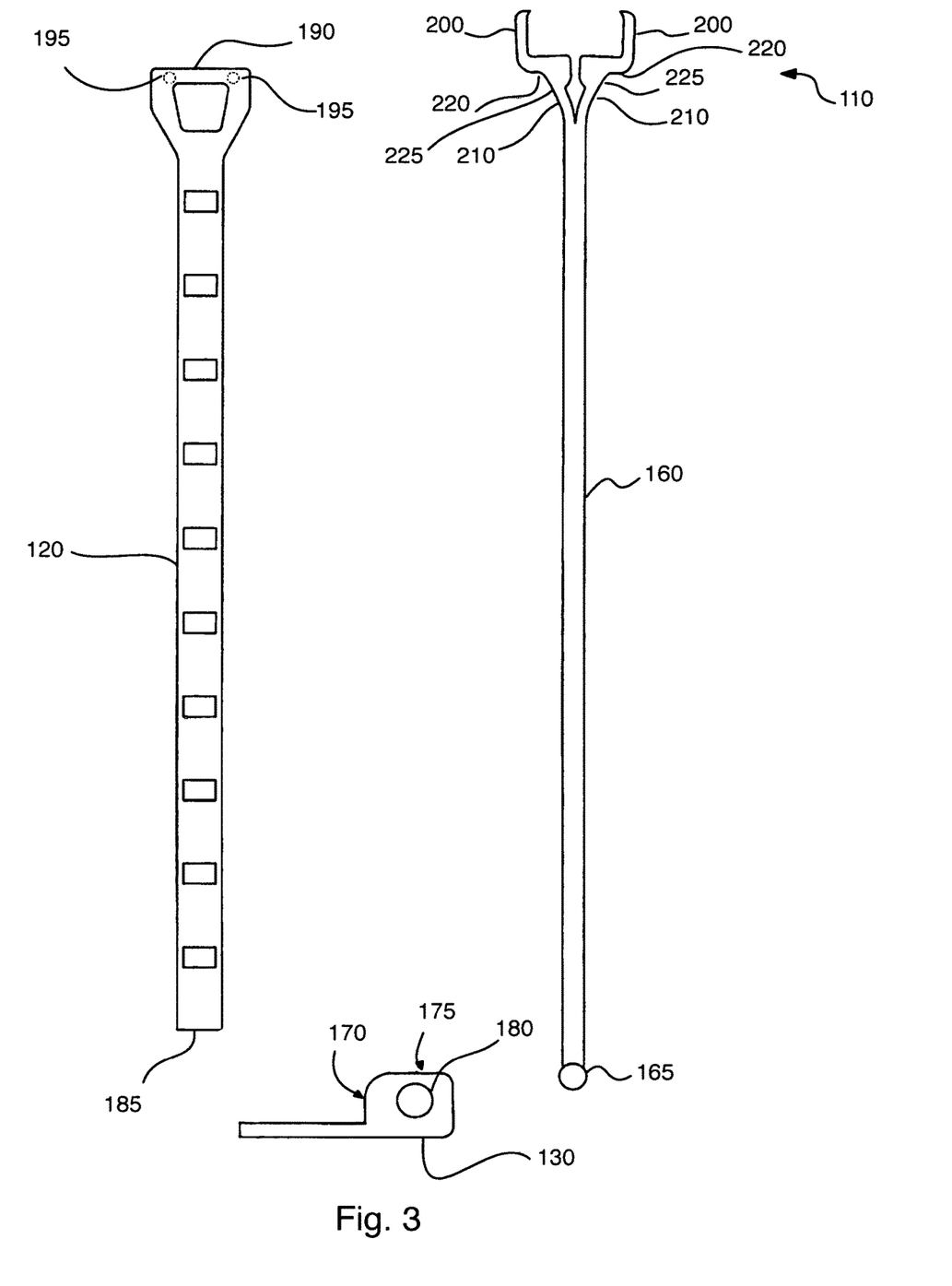
FIG. 3 is an exploded view of an embodiment of the present invention.

Turning now to FIG. 3, there is shown an exploded view of the insertion instrument 100. The device holder 110 has an inner shaft 160 with a shaft pin 165 at the proximate end. The locking lever 130 has a locking lever pivot 180 that rotatably engages the shaft pin 165 when assembled and a deployed cam surface 170 and an undeployed cam surface 175. The housing 120 has a housing cam following surface 185 that engages with the undeployed cam surface 175 of the locking lever 130 when the insertion instrument 100 is in an undeployed condition and engages with the deployed cam surface 170 of the locking lever 130 when the insertion instrument is in the deployed condition.

Still with reference to FIG. 3, the housing 120 has a housing locking surface 190 at the distal end from the housing cam following surface 185 with optional device locking cam surface members 195. The device holder 110 has a device holder locking surface 220 that engages with the housing locking surface 190 when the insertion instrument 100 is in a deployed condition. The device holder 110 can optionally have a device holder cam following surface 225 that would engage with the optional device locking cam surface members 195 if so provided to close the device holder 110 when transitioning from the undeployed condition to the deployed condition, or when transitioning from the deployed condition to the undeployed condition. The device holder 110 has a device holding member 200 and a device holder flexible shaft 210 that cooperates to hold or release the device depending on the state of the insertion instrument 100 in either a deployed condition or an undeployed condition.

Figure 4:
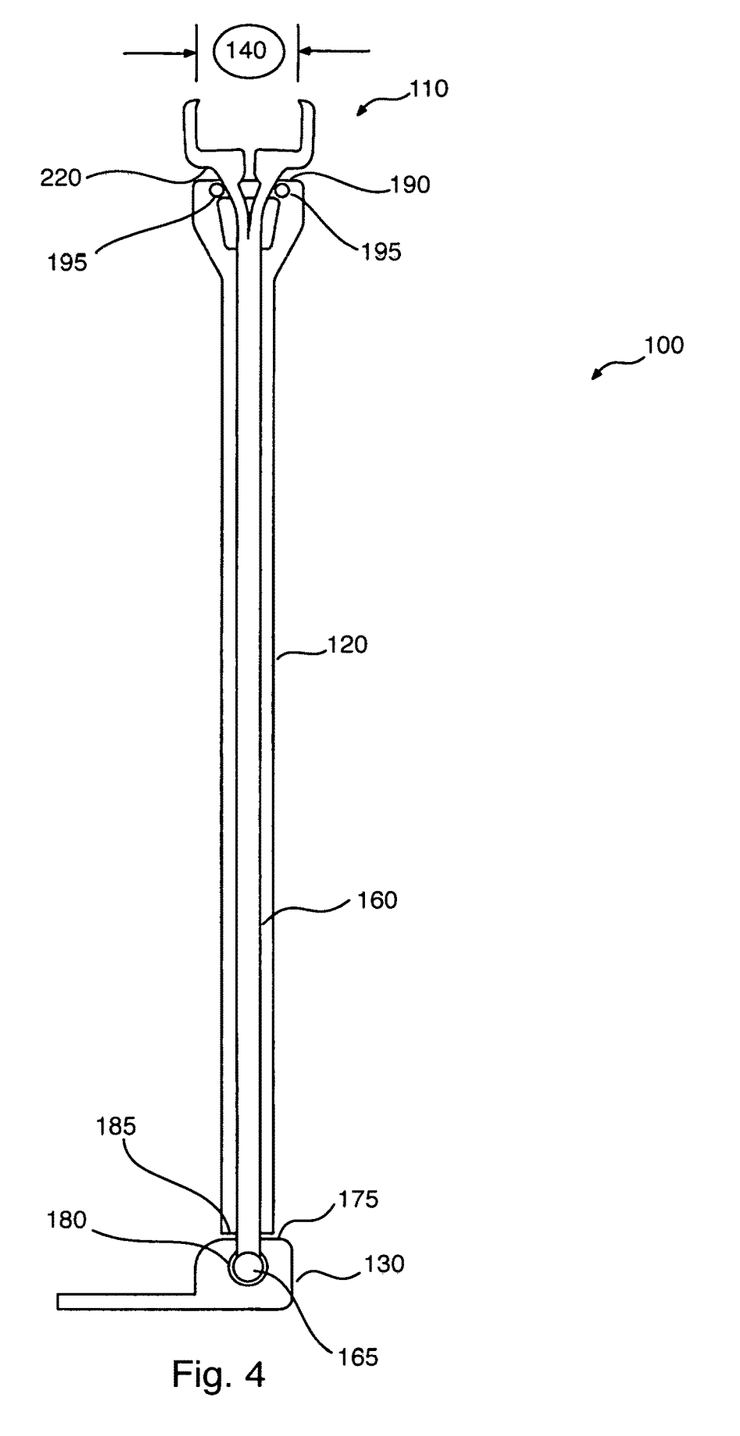
FIG. 4 is a partial cutaway view of an embodiment of the present invention in an undeployed state.

Turning now to FIG. 4, the insertion instrument 100 is shown in a partial cutaway view in an undeployed condition. Locking lever 130 is positioned with its undeployed cam surface 175 in proximity to, but not necessarily in contact with, the housing cam following surface 185. Shaft pin 165 is loosely engaged at the locking lever pivot 180 such wherein the inner shaft 160, fixedly attached to the shaft pin 165, is not fixedly engaged within the housing 120. Accordingly, the device holder locking surface 220 is not engaged with the housing locking surface 190 so that the device holder 110 exhibits an undeployed device spacing 140 that permits placement of the device in the device holder 110 or removal of the device from the device holder 110.

Still referring to FIG. 4, the optional device locking cam surface members 195 if so provided, are positioned so that the inner shaft 160, when in the undeployed condition, is not constrained so that the undeployed spacing 140 permits placement of the device in the device holder 110 or removal of the device from the device holder 110.

Figure 5:
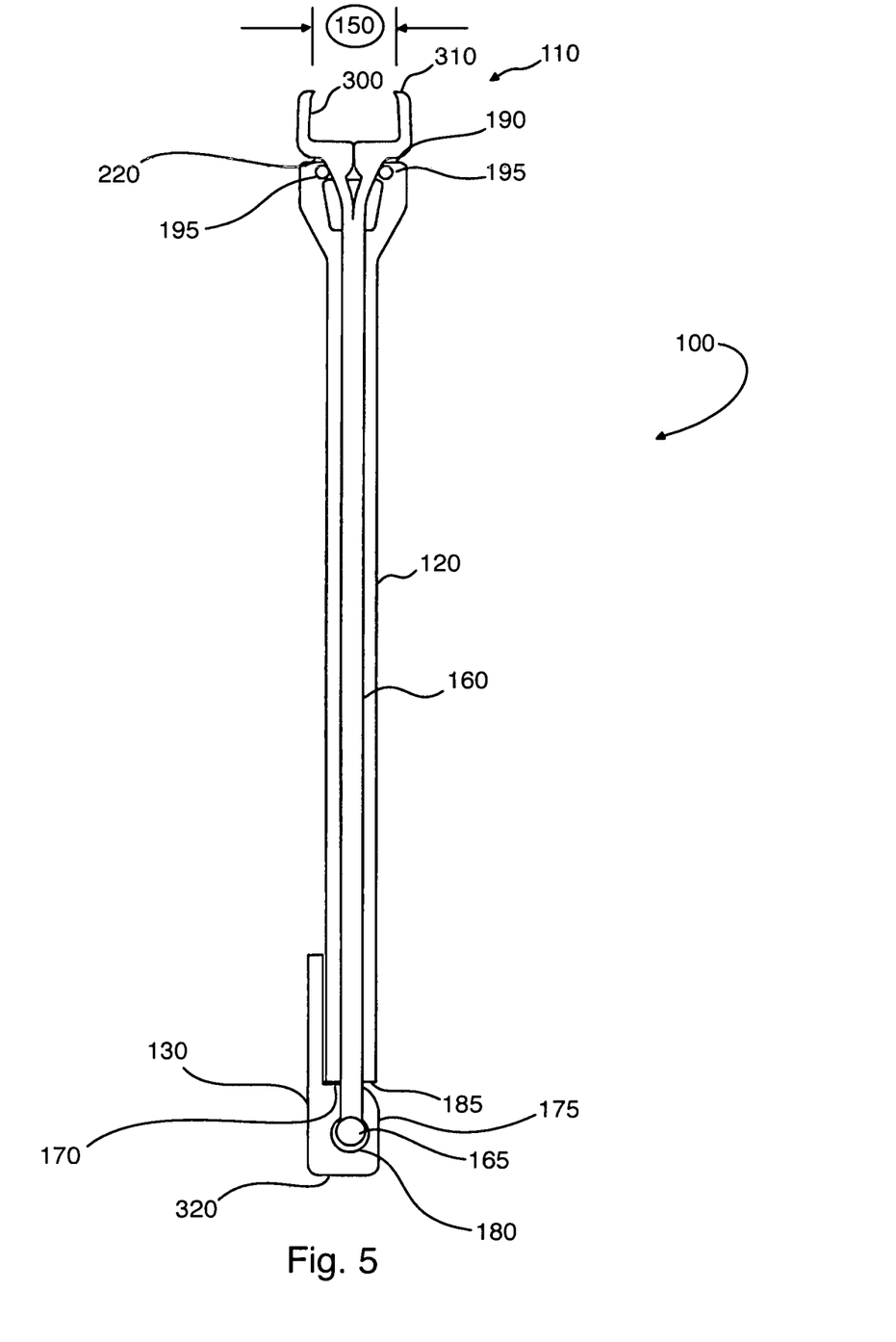
FIG. 5 is a partial cutaway view of an embodiment of the present invention in a deployed state.

Turning now to FIG. 5, the insertion instrument 100 is shown in a partial cutaway view in a deployed condition. Locking lever 130 is positioned with its deployed cam surface 170 in contact with the housing cam following surface 185. In this position, the shaft pin 165 constrained within the locking lever pivot 180 is displaced distally from the housing cam following surface 185. Accordingly, the inner shaft 160 is relatively translated within the housing 120 so that the device holder locking surface 120 is in contact with the housing locking surface 190 causing the device holder 110 to be in the deployed condition with a deployed spacing 150. In the deployed condition the device gripping surface 300 makes contact with the device securely holding it in the device holder 110. The amount of relative translation of the inner shaft 160 is proportional to the difference in thickness from the cam locking pivot 180 to the deployed cam surface 170 and the undeployed cam surface 175. The device holder 110 can include device holder gripping extensions 310 that provide additional device holding properties that would resist extraction of the device while the insertion instrument 100 is in the deployed condition.

Still referring to FIG. 5, the optional device locking cam surface members 195 if so provided, are positioned so that the inner shaft 160, when in the deployed condition, is constrained so that the deployed spacing 150 securely holds a device in the device holder 110 and resists removal of the device from the device holder 110.

Further, with reference to FIG. 5, when the insertion instrument 100 is in the deployed condition, with the locking lever 130 in the deployed position, and deployed cam surface 170 in contact with the housing cam following surface, the impact surface 320 can be used to apply force, including impact force from a hammer to assist with insertion of the device into the vertebral space during surgery.

Of course, the insertion instrument may have more than one deployed configuration as well as more than one undeployed configuration as the system permits varying degrees of deployment according to surgeon preference. Also, the deployment is reversible such that the locking lever 130 can be disengaged thereby releasing the device from the device holder 110.

Figure 6:
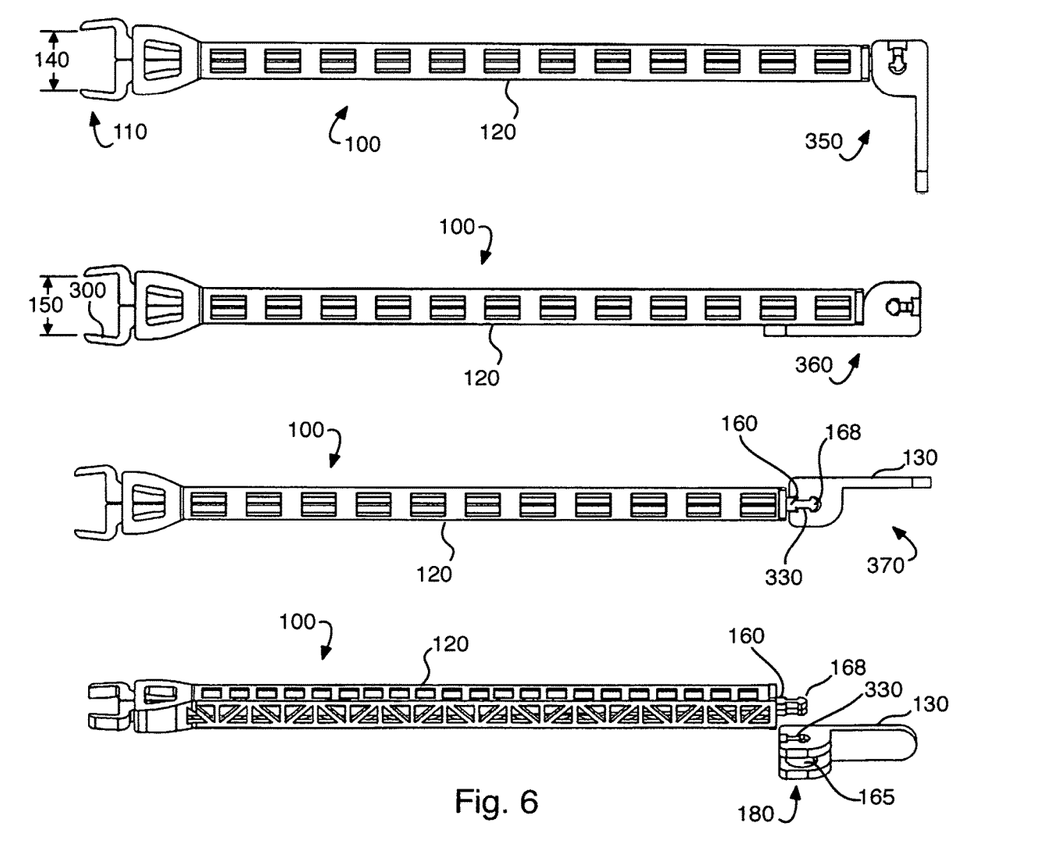
FIG. 6 depicts an embodiment of the present invention in four representative configurations including an undeployed condition, a deployed condition, an extraction condition, and a disassembled condition.

In an embodiment of the invention, the insertion instrument 100 can be disassembled during use to provide for extraction of the insertion instrument 100 after insertion of the device into the vertebral space so that the position of the device is not altered during extraction of the insertion instrument 100. Referring now to FIG. 6, an embodiment of the invention is shown with the locking lever 130 in at least three positions: the undeployed position 350; the deployed position 360; and the extraction position 370. In the undeployed position 350, as described above, the device holder 110 exhibits an undeployed device spacing 140 that permits placement of the device in the device holder 110 or removal of the device from the device holder 110. In the deployed position 360, as described above, the device holder 110 exhibits a deployed device spacing 150 so that the gripping surface 300 makes contact with the device securely holding it in the device holder 110 for insertion into the vertebral space. In the extraction position 370 the locking lever 130 can be removed from the inner shaft 160 (partially obscured) to permit removal of the housing 120 from the inner shaft 160. In this embodiment, the shaft pin 165 is not fixedly attached to the inner shaft 160. In this embodiment, the inner shaft has a key pin 168 having a shape profile of a slot 330 in the locking lever 130 and engages the shaft pin 165, whereby the shaft pin 165 rotates within the locking lever 130 about the pivot point 180.

While insertion instrument 100 can be provided for disassembly with the locking lever 130 in any of the undeployed position 350, the deployed position 360 and/or the extraction position 370, it can be advantageous to restrict disassembly in only in the extraction position 370 to prevent inadvertent disassembly during use of the insertion instrument 100, i.e., during preparation and insertion of the implant.

Figure 7:
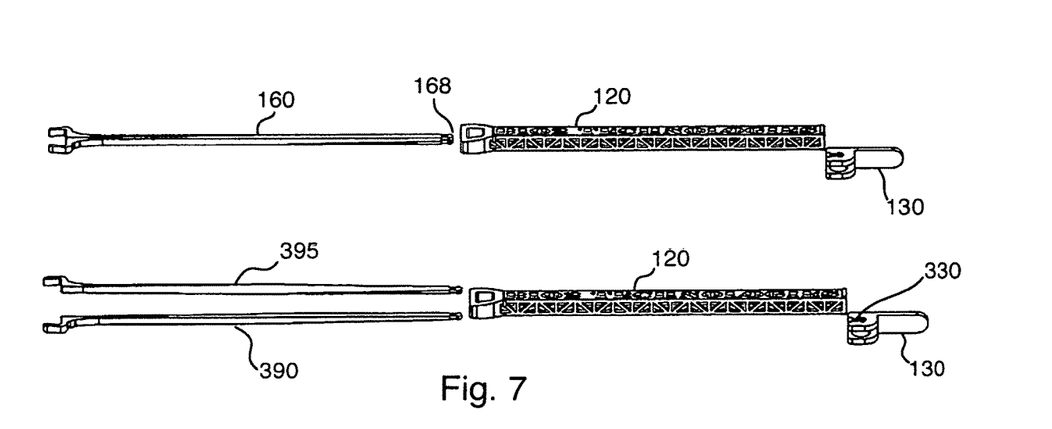
FIG. 7 depicts an embodiment of the present invention in two views showing the sequence for disassembly of the insertion instrument.

Referring now to FIG. 7, which further depicts the embodiment of the insertion instrument 100 as depicted in FIG. 6, the locking lever 130 is removable in the undeployed condition to permit removal of the inner shaft 160 from the housing 120. The locking lever 130 can be removed in the undeployed condition for disassembly of the insertion instrument 100 or as shown, the key pin 168 on the inner shaft 160 can be disengaged from the shaft pin 165 (not shown) when the locking lever is in the extraction position 370. The slot 330 is provided to permit removal of the inner shaft 160 when the locking lever 130 in the extraction position 370. In yet another embodiment, the inner shaft 160 can be bifurcated in at least two sections, as shown in FIG. 7 as the first section 390 and the second section 395, so that during extraction of the insertion instrument 100 from the intervertebral space the device holder 110 can be removed as a plurality of sections to further reduce the potential for displacement of the implant in the vertebral space.

Figures 8, 9:
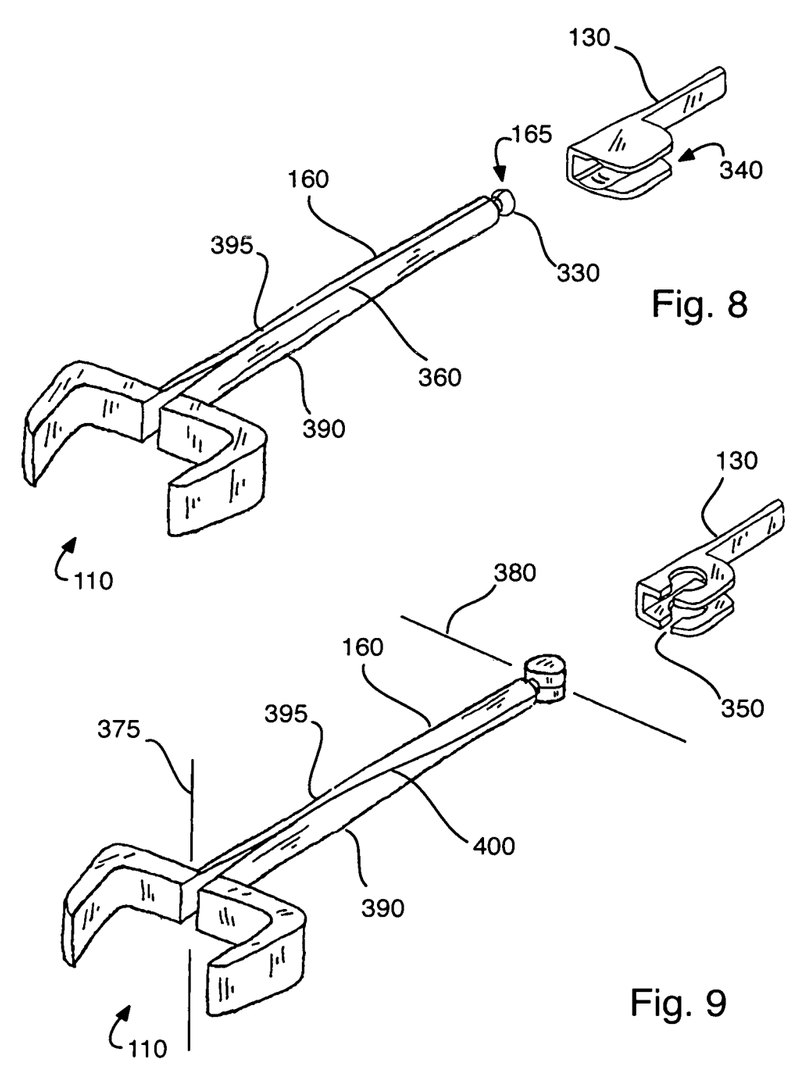
FIG. 8 is an exploded isometric view of certain aspects of an embodiment of the present invention.
FIG. 9 is an exploded isometric view of an alternate embodiment of certain aspects of the embodiment of the present invention depicted in FIG. 8.

FIG. 8 depicts the device holder 110 and inner shaft 160 of an embodiment of the insertion instrument 100 of FIG. 7, showing the first section 390 and the second section 395. In this embodiment, the shaft pin 165 is a spherical member 330 that engages with a socket 340 in locking lever 130. The inner shaft 160 is fabricated in at least two sections with a shaft seam 360 running the length through the center of the inner shaft 160. The cross section of the inner shaft 160 can be rectangular, cylindrical as shown, or any cross-sectional shape to fit within the housing 120 (not shown for clarity).

FIG. 9 depicts an embodiment of the device holder 110 and inner shaft 160 of FIG. 8 with a spiral shaft seam 400 running the length through the center of the inner shaft 160 from the device holder parting plane 375 to the distal plane 380. In this embodiment the shaft pin 165 is separated perpendicular to its axis for ease in assembly by permitting insertion of the shaft pin 165 into the locking lever 130 in the extraction position using slot 350 with the bifurcated shaft pin in a stacked alignment.

The insertion instrument can also be used to remove a device from the patient or to adjust its position following deployment. In such a case, the insertion instrument is inserted into the vertebral space in an undeployed configuration and deployed to capture the device, and then retracted from the vertebral space to remove the device. Similarly, the insertion instrument can be adapted to capture the device in a disassembled configuration and assembled in place to extract the implant.

In typical applications, the insertion instrument includes a variety of markings, for example, to indicate various status conditions of the tool and the associated device. In an alternative arrangement, the markings are selected as conventional visible markings or may be radio-opaque. The insertion instrument may also be optionally arranged with one or more markers selected, for example, from ultrasonic, magnetic markers or other marker types to advantageously avoid the need for fluoroscopy.

Fabrication of the insertion instrument 100 can be performed by conventional machining methods using stainless steel, or biocompatible plastic materials such as nylon or polycarbonate by machining or molding each component and assembling the components into the insertion instrument 100. Alternatively, the insertion instrument 100 can be fabricated as a completed as a completely functional assembled unit using three-dimensional printing methods that include the use of struts, or temporary support elements, to support elements that are not stationary relative to adjacent elements once the fabrication is completely printed. When fabricated as a completely functional assembled unit, using three-dimensional printing methods, the instrument 100 requires no additional assembly or handwork to be completely functional. Further, if the starting materials of the three-dimensional printer are kept in a clean state prior and during processing, the heat generated during the three-dimensional printing process is generally hot enough so as to meet the requirements of providing the completed instrument 100 in a sterile form as it leaves the three-dimensional printer.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

The invention claimed is:

1. An orthopedic implant insertion instrument for inserting an implant in an intervertebral space, the orthopedic implant insertion instrument comprising:
    a housing having a distal end and a proximate end;
    a device holder having a gripping surface and a shaft, the shaft having a shaft pin, the device holder adapted to capture the implant using the gripping surface in an intervertebral space;
    the distal end of the housing having a locking surface that engages the device holder;
    a locking lever rotatably engaged with the shaft pin, the locking lever having a cam surface that engages with the proximate end of the housing to translate the shaft when rotated about the shaft pin;
    wherein the length of the shaft corresponds to the length of the housing so that the gripping surface engages the implant when the locking lever translates the shaft, and wherein the locking lever is removable, and the locking lever further comprises a slot that restricts removal to a specific orientation of the locking lever to the inner shaft.

2. The orthopedic implant insertion instrument according to claim 1 wherein the locking lever further comprises an impact surface that is aligned with the shaft when the cam surface is engaged with the proximate end of the housing whereby an impact force applied to the impact surface is transmitted through the orthopedic implant insertion instrument to the implant in an intervertebral space.

3. The orthopedic implant insertion instrument according to claim 1 wherein the gripping surface is released when the locking lever is rotated to disengage the cam surface from the proximate end of the housing.

4. The orthopedic implant insertion instrument according to claim 1 wherein the distal surface of the housing further comprises a cam surface that engages with the device holder when the locking lever translates the shaft.

5. The orthopedic implant insertion instrument according to claim 1 wherein the inner shaft is bifurcated with a parting line running through a central axis.

6. The orthopedic implant insertion instrument according to claim 4 wherein the inner shaft is bifurcated with a parting line running through a central axis.

7. The orthopedic implant insertion instrument according to claim 2 wherein the distal surface of the housing further comprises a cam surface that engages with the device holder when the locking lever translates the shaft.

8. The orthopedic implant insertion instrument according to claim 1 wherein the inner shaft is bifurcated with a parting line running through a central axis.

9. The orthopedic implant insertion instrument according to claim 8 wherein the parting line running through the central axis is a spiral.

10. The orthopedic implant insertion instrument according to claim 1 wherein the shaft pin is spherical.

11. The orthopedic implant insertion instrument according to claim 1 wherein the instrument is fabricated from at least one of stainless steel, nylon and polycarbonate.

12. The orthopedic implant insertion instrument according to claim 1 wherein the instrument is fabricated as a functional assembled unit using three-dimensional printing methods and further comprising struts to support the inner shaft to the housing.

* * * * *